United States Patent [19]
Yamamoto et al.

[11] Patent Number: 6,071,702
[45] Date of Patent: Jun. 6, 2000

[54] PROBE-BEARING ELEMENT AND METHOD FOR PRODUCING THE SAME

[75] Inventors: Kenji Yamamoto; Noriko Yurino; Hisanori Nasu, all of Kanagawa, Japan

[73] Assignee: Hitachi Software Engineering Co., Ltd., Tokohama, Japan

[21] Appl. No.: 09/364,752

[22] Filed: Jul. 30, 1999

[30] Foreign Application Priority Data

Sep. 4, 1998 [JP] Japan .................................. 10-250897

[51] Int. Cl.⁷ ............................... C12Q 1/68; C12Q 1/70; C12P 19/34; C07H 21/02; C07H 21/04
[52] U.S. Cl. ..................... 435/6; 435/6; 435/5; 435/91.2; 435/23.1; 435/24.3
[58] Field of Search ................................... 435/6, 5, 91.2; 536/23.1, 24.3, 24.33, 25.3

*Primary Examiner*—John S. Brusca
*Assistant Examiner*—Jeffrey S. Lundgren
*Attorney, Agent, or Firm*—Fish & Richardson P.C.

[57] ABSTRACT

A probe-bearing element according to the present invention includes a sheet-like body having a plurality of through holes which each bears a biopolymer probe. The sheet-like body may have a thickness of 100 $\mu$m to 2 mm, and may be made of glass, acrylic resin, metal or plastic. Preferably, the size of the through hole is about 10–100 $\mu$m in diameter considering the number of samples relative to the size of the element, amounts of probes required for hybridization and the detection sensitivity. The plurality of through holes are preferably arranged in concentric circles or in a spiral.

69 Claims, 6 Drawing Sheets

PROBE-BEARING ELEMENT AND METHOD FOR PRODUCING THE SAME

FIELD OF THE INVENTION

The present invention relates to a probe-bearing element that bears probes for detecting DNA or protein in a sample through hybridization reaction, and to a method for producing the probe-bearing element.

BACKGROUND OF THE INVENTION

In the fields of molecular biology and biochemistry, biopolymers such as nucleic acids and proteins from organisms are identified and fractionated in order to search useful genes or to diagnose diseases. As a pre-treatment of such identification and fractionation, a hybridization reaction is often employed in which a target molecule in a sample is hybridized with a nucleic acid or a protein of a known sequence. For this purpose, a probe-bearing element known as a biochip, a DNA disc or the like is used which bears probes such as DNA, RNA, protein and the like with known sequences at predetermined positions.

The probe-bearing element is provided with a plurality of features that are bound with diverse probes, respectively. The probe-bearing element is placed in a reaction vessel called a chamber together with sample DNA such that the sample DNA labeled with fluorescence hybridizes with the probes bound to the features of the probe-bearing element. Then, the probe-bearing element is irradiated with excitation light, thereby detecting fluorescence intensity at each feature to determine an amount of binding between each probe and the sample DNA. The results can be used as advantageous information.

Conventionally, as described in U.S. Pat. No. 5,445,934, a probe-bearing element is generally produced one by one at a time by synthesizing a protein or a DNA probe of interest on a feature of the probe-bearing element. Such conventional method is troublesome and time-consuming, and thus increases the cost of the probe-bearing element. As a result, probe-bearing elements are unsuitable to be generally used in, for example, hospitals for diagnosing genetic diseases. Moreover, since the synthesis has limitation in producing long probes, the types of DNA used as probes are also limited.

The present invention was accomplished in view of the above problems, and aims at providing a probe-bearing element which can be mass produced and which has a stable quality, and a method for producing the probe-bearing element.

SUMMARY OF THE INVENTION

A probe-bearing element according to the present invention includes a sheet-like body having a plurality of through holes which each bears a biopolymer probe. The sheet-like body may have a thickness of 100 μm to 2 mm, and may be made of glass, acrylic resin, metal or plastic. Preferably, the size of the through hole is about 10–100 μm in diameter considering the number of samples relative to the size of the element, amounts of probes required for hybridization and the detection sensitivity. The plurality of through holes are preferably arranged in concentric circles or in a spiral.

The through holes bear various types of probe, respectively. At least one of the probes may have a length of 200 bases or more. The probe may be DNA, RNA or a protein.

At least one surface of each of the sheet-like bodies may be applied with an adhesive. It is also possible that neither surface of the sheet-like bodies have an adhesive thereon.

In one aspect, the present invention is a method for producing a sheet-like probe-bearing element having a plurality of through holes bearing biopolymer probes, including the steps of: piling a plurality of sheet-like bodies; providing a plurality of through holes through the pile of sheet-like bodies; injecting a biopolymer probe into each of the through holes; and separating the sheet-like bodies from each other.

In another aspect, the present invention is a method for producing a sheet-like probe-bearing element having a plurality of through holes bearing biopolymer probes, including the steps of: providing a plurality of through holes through a block-like material; injecting a biopolymer probe into each of the through holes; and slicing the block-like material into sheets such that every sheet has the plurality of through holes.

The pile of sheet bodies or the block material may be provided with through holes through laser irradiation. The through holes are preferably pretreated in order to promote binding between the through holes and the probes, before injecting the probes into the through holes. The pretreatment can be conducted by coating the through holes with poly-1-lysine or carbodiimide (Japanese Patent Laid-Open Application No. 8-23975).

DETAILED DESCRIPTION OF THE INVENTION

Hereinafter, the present invention will be described in more detail by way of examples with reference to the accompanying drawings.

Figure 1:
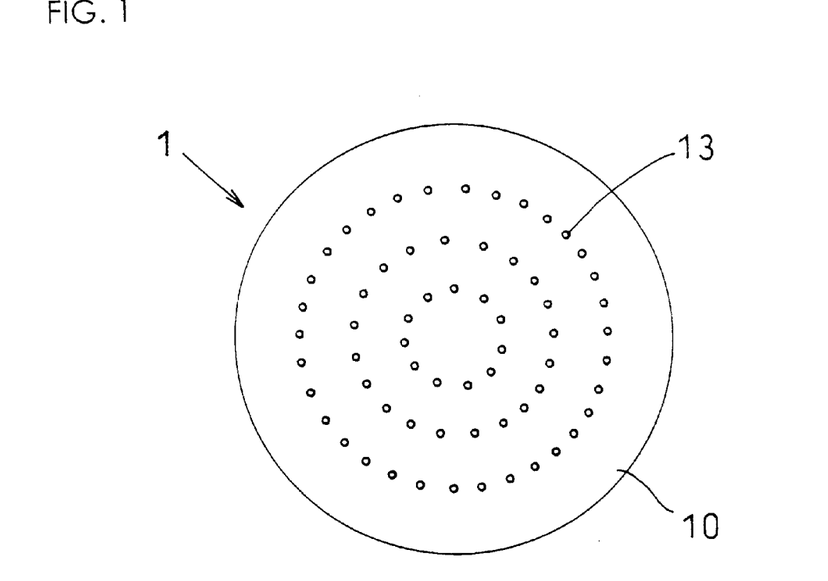
FIG. 1 is a schematic plan view showing an exemplary probe-bearing element according to the present invention.
Figure 2:
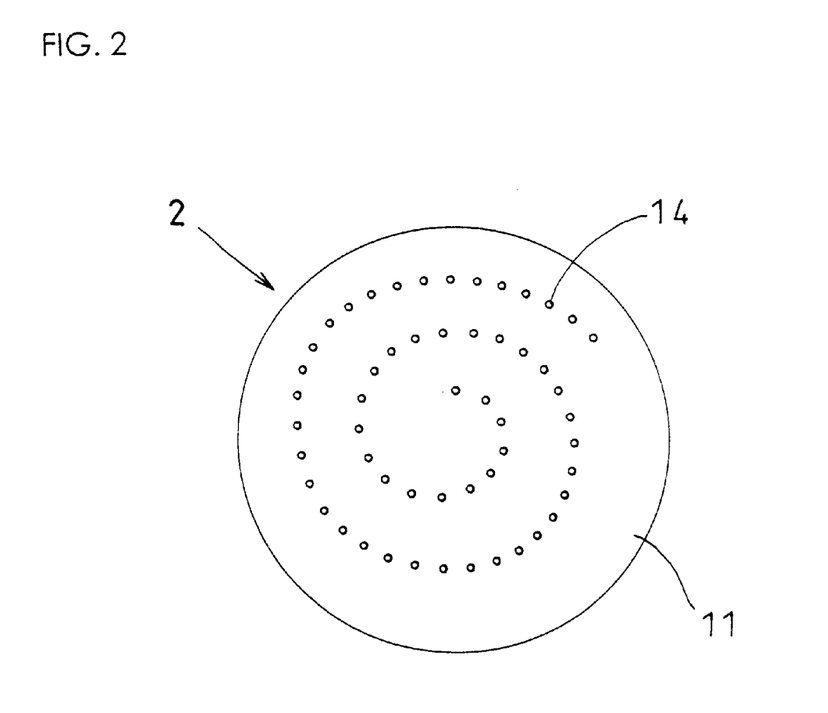
FIG. 2 is a schematic plan view showing another exemplary probe-bearing element according to the present invention.

FIGS. 1 and 2 are schematic plan views showing exemplary probe-bearing elements 1 and 2 according to the present invention, respectively. The probe-bearing element 1 shown in FIG. 1 has a circular main body 10 with a plurality of through holes 13 arranged in concentric circles. Each of the plurality of through holes 13 bears a biopolymer probe. The probe-bearing element 2 shown in FIG. 2 has a circular main body 11 with a plurality of through holes 14 arranged in a spiral. Again, each of the plurality of through holes 14 bears a biopolymer probe. The shape of the probe-bearing element is not limited to circle as shown in FIGS. 1 and 2, and may be a polygon such as a square or a hexagon.

Figure 3:
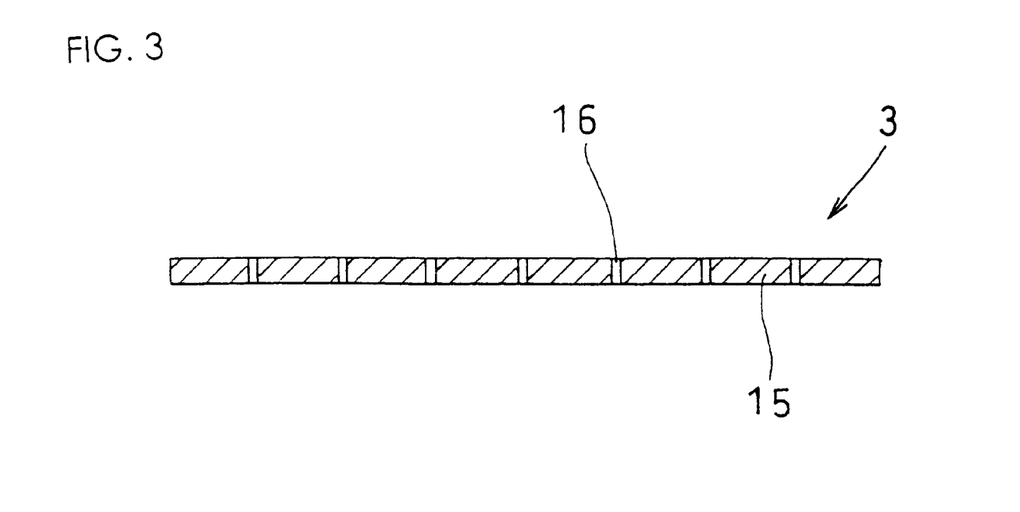
FIG. 3 is a schematic cross-sectional view showing an exemplary probe-bearing element according to the present invention.
Figure 4:
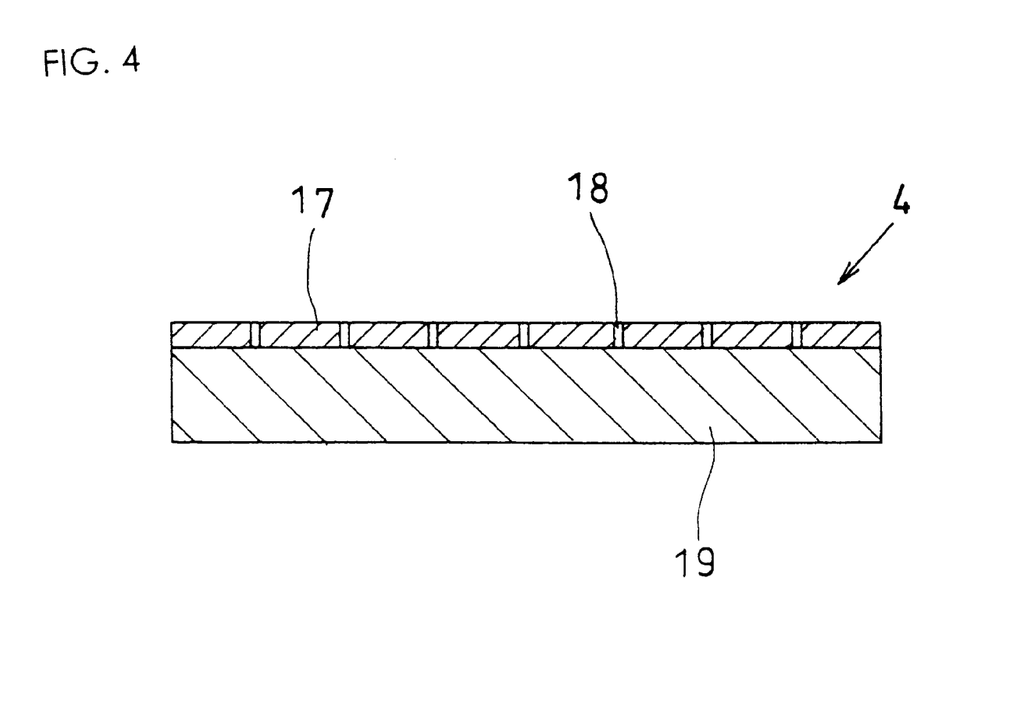
FIG. 4 is a schematic cross-sectional view showing another exemplary probe-bearing element according to the present invention.

FIGS. 3 and 4 are schematic cross-sectional views showing exemplary probe-bearing elements 3 and 4 according to the present invention, respectively. The probe-bearing element 3 shown in FIG. 3 has a sheet-like main body 15 that has a plurality of through holes 16 passing therethrough. The probe-bearing element 4 shown in FIG. 4 has a sheet-like body 17 with a plurality of through holes 18 passing therethrough and has a reinforcement member 19 adhered to the bottom surface of the sheet-like body 17 with, for example, an adhesive.

The sheet-like bodies 15 and 17 may be made of a material which does not denature at a temperature as high as about 100° C. and at a humidity as high as about 100%, for example, glass, metal such as stainless steel or aluminum, plastic such as polycarbonate, polyethylene or polypropylene, an acrylic resin, or the like. The thickness of the sheet-like bodies 15 and 17 is suitably about 100 μm to 2 mm. The reinforcement member 19 is provided for providing physical reinforcement of the sheet-like body 17 and for facilitating the handling of the probe-bearing element 4. The reinforcement member 19 may be a glass plate, a plastic plate, an aluminum plate or the like with a thickness of about 1 mm to 5 mm. The reinforcement member 19 is adhered to the sheet-like body 17 with an adhesive such as an acrylic resin adhesive, an ethylene-vinylacetate adhesive or an elastomer adhesive.

The size of the through holes 13, 14, 16 and 18 is about 10 μm to 100 μm diameter. Each of the through holes 13, 14, 16 and 18 bears in its interior (inner wall), a probe that is capable of hybridizing with a biopolymer such as DNA, RNA, protein or the like with specific sequences. Whereas the types (lengths) of the probe DNA are limited in a conventional method, the probe-bearing element of the present invention can use any type of DNA as the probe regardless of its length.

Hereinafter, an exemplary of a method for producing a probe-bearing element of the present invention will be described. In this example, a sheet-like body is made from polypropylene.

Figure 5:
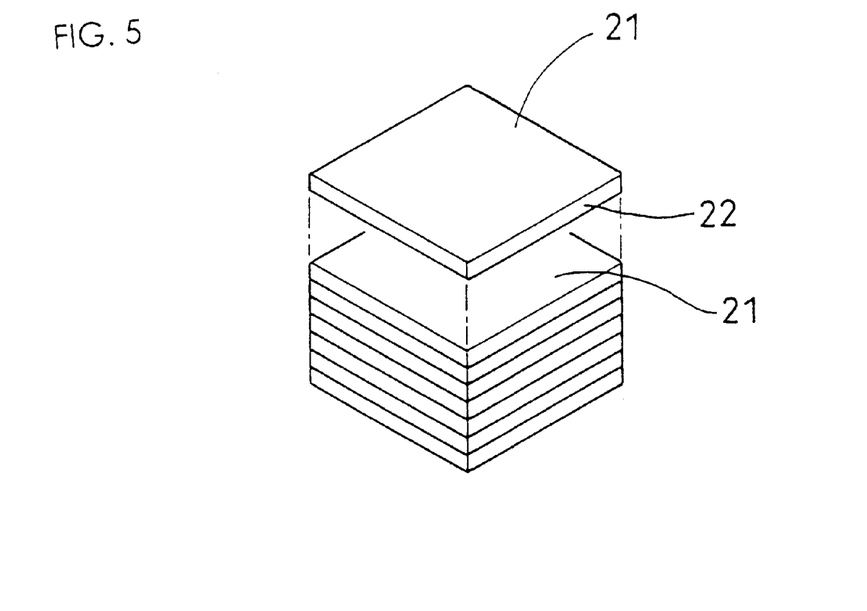
FIG. 5 is a perspective view for illustrating one of the steps in the method for producing a probe-bearing element of the present invention.

FIG. 5 is a perspective view for illustrating one of the steps in the method for producing the probe-bearing element of the present invention. About several tens to several hundreds of polypropylene sheets 22 (thickness: about 100 μm) are piled and adhered to each other with a thin layer of adhesive 21 applied therebetween. The number of the polypropylene sheets 22 is suitably selected depending on a type and an output of laser used for the laser process described later. For example, $CO_2$ laser with an output of 0.2 kW can cut various types of resin with a thickness of about 3 mm. Thus, this laser can provide a through hole through a maximum of 30 polypropylene sheets at a time. The adhesive is, for example, an elastomer adhesive that easily peels off with external force.

Figure 6:
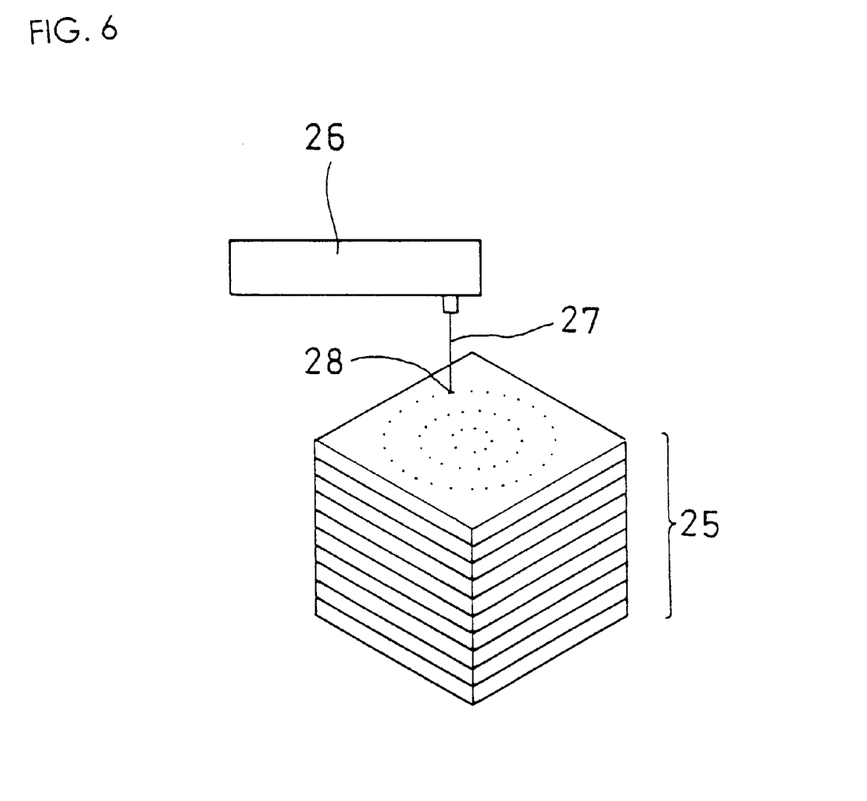
FIG. 6 is a perspective view for illustrating one of the steps in the method for producing the probe-bearing element of the present invention.

FIG. 6 is a perspective view for illustrating one of the steps in the method for producing the probe-bearing element of the present invention. A plurality of through holes 28 are provided through the pile of sheets 25 by a laser beam 27 radiated from a laser processor 26. The laser processor 26 may employ, for example, ruby laser, neogium glass laser, $CO_2$ laser or YAG laser. The diameter of each through hole 28 provided with the laser processor 26 is about 10 to 100 μm. The through holes 28 are arranged in concentric circles or in a spiral as shown in FIGS. 1 and 2, respectively.

Then, the pile of polypropylene sheets 25 with the through holes 28 is pretreated in order to promote the binding between the inner walls of the through holes 28 and biopolymer probes to be applied. The pretreatment may be conducted, for example, by coating the inner walls of the through holes 28 with poly-1-lysine or with carbodiimide. Coating with poly-1-lysine is conducted as follows. First, the pile of polypropylene sheets 25 is immersed and shaken in a poly-1-lysine solution at 18–26° C. for 5 minutes. Then, the pile of polypropylene sheets 25 is taken cut from the poly-1-lysine solution, placed in an oven at 60° C. for 1 hour and finally cooled to room temperature. The carbodiimide coating is conducted by immersing and shaking the pile of polypropylene sheets 25 in a carbodiimide solution.

Thereafter, a biopolymer probe is injected into each through hole 28 of the pile of polypropylene sheets 25 according to any method. For example, probe DNA is drawn in a syringe with a fine needle that can be inserted into the through hole 28 to thereby inject the probe DNA. Alternatively, the probe DNA may be drawn out from the syringe by vacuum suction from the side opposite to the side of inserting the syringe.

Figure 7:
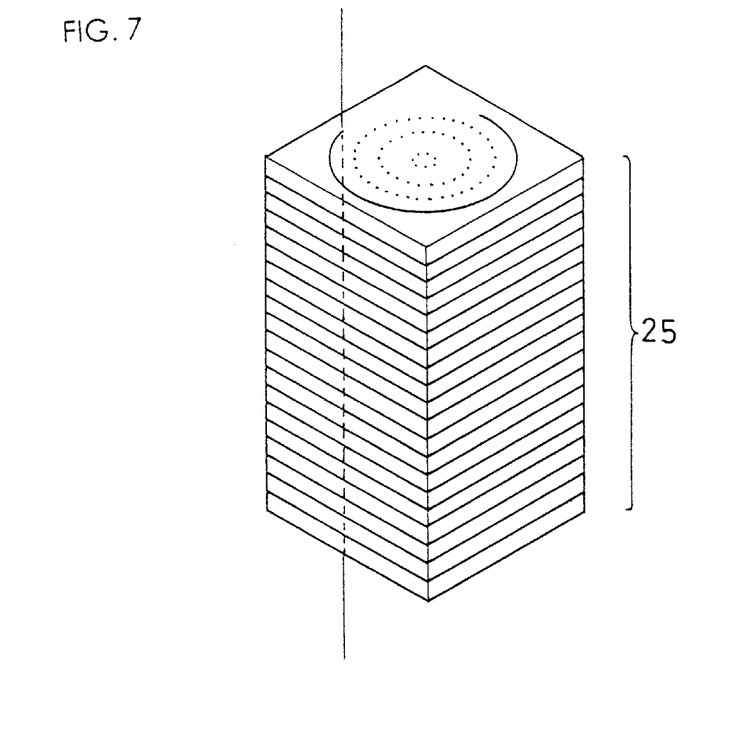
FIG. 7 is a perspective view for illustrating one of the steps in the method for producing the probe-bearing element of the present invention.
Figure 8:
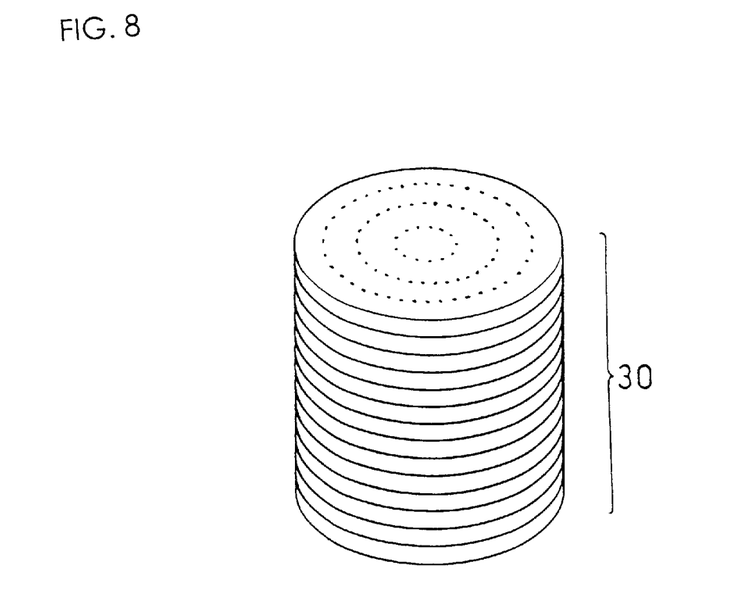
FIG. 8 is a perspective view for illustrating one of the steps in the method for producing the probe-bearing element of the present invention.

Then, as shown in FIG. 7, the pile of polypropylene sheets 25 is cut into a columnar block 30 (FIG. 8) with a diameter of about 2 cm using a laser processor, a wire saw or the like. The cutting step shown in FIG. 7 may be conducted prior to the step of pretreating the through holes 28 for promoting the binding between the through holes 28 and the biopolymer probes or prior to the step of injecting the probes into the through holes 28.

Finally, the polypropylene sheets 22 with the biopolymer probes are separated from each other.

Thus, identical probe-bearing elements with diverse probes at the same positions can be mass-produced. By changing the type and the power of the laser, the number of sheets processed at a time can be adjusted while more than several hundreds of probe-bearing elements can be produced at a time. The polypropylene sheet 22 may be used by itself as a probe-bearing element, or it may be adhered to a reinforcement member (such as a glass, plastic or metal plate, or the like with a thickness of about 1–5 mm) to provide physical reinforcement and easy handling as described above with reference to FIG. 4.

Figure 9A:
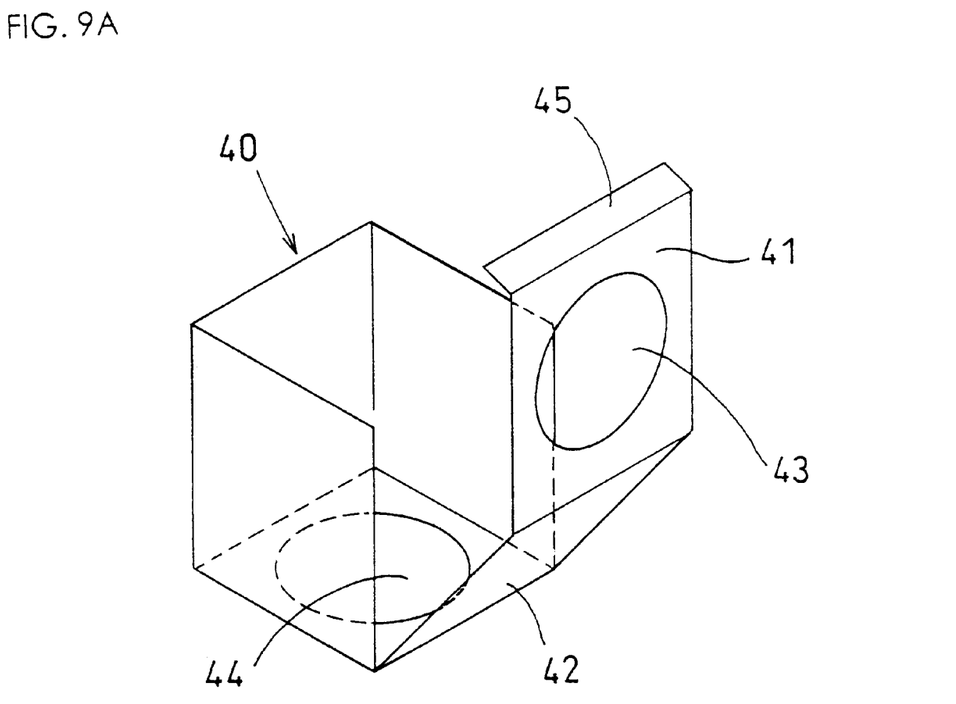
FIGS. 9A and 9B are schematic views showing an example of a securing member for securing a plurality of sheets.
Figure 9B:
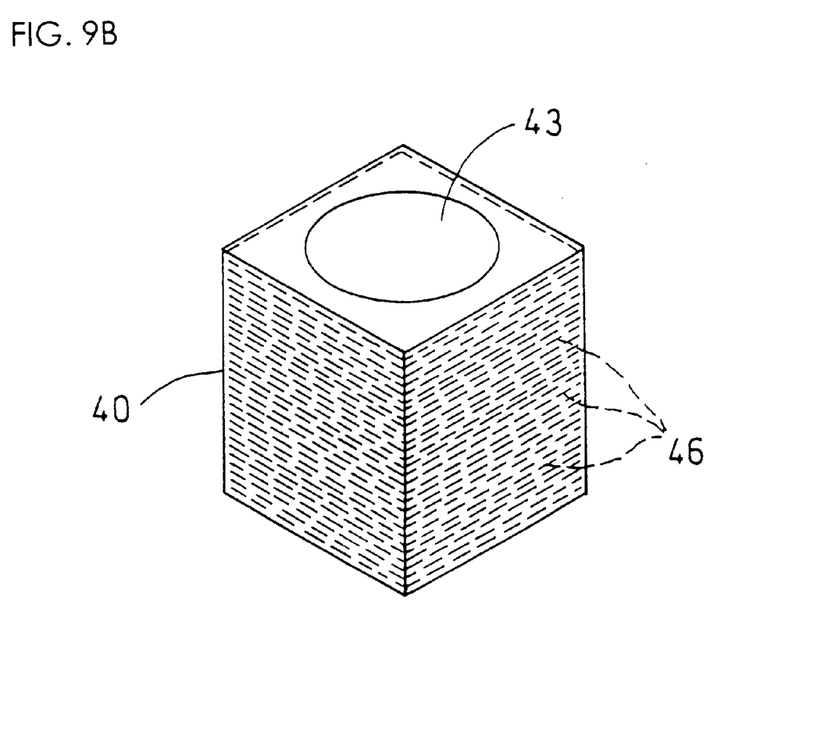

It may not be necessary to adhere each of the polypropylene sheets to each other with an adhesive upon processing if they can be secured mechanically with a securing member or the like. FIGS. 9A and 9B are schematic views showing an example of a securing member 40 for securing a plurality of sheets without an adhesive. The box-like securing member 40 has an inner space for accommodating a predetermined number of sheets 46. As shown in FIG. 9A, the box-like securing member 40 is openable at planes 41 and 42. The upper plane 41 and a bottom plane facing thereto are provided with circular openings 43 and 44, respectively. The size of the circular openings 43 and 44 is determined such that exposed surfaces of the sheets through the openings 43 and 44 are greater than the area to be provided with the through holes 28 with the laser processor 26 (FIG. 6).

Specifically, the planes 41 and 42 are unfolded to put a predetermined pile of sheets in the securing member 40. Then, the planes 41 and 42 are refolded to form a box as shown in FIG. 9B. A flap 45 is, for example, applied with an adhesive to seal the box so that the sheets 46 do not move within the securing member 40. The area of the sheet 46 exposed through the opening 43 is subjected to the laser processing described above with reference to FIG. 6 to provide a plurality of through holes 28 in concentric circles or in a spiral. As described above, the inner walls of the thorough holes 28 are coated with poly-1-lydine or carbodiimide before injecting biopolymer probes into the through holes 28.

Figure 10:
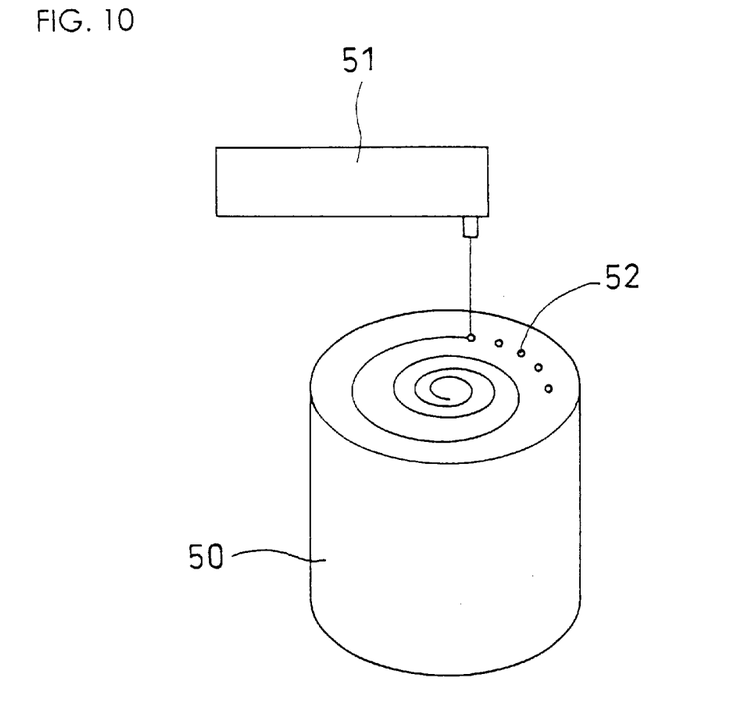
FIG. 10 is a schematic view showing one of the steps in another exemplary method for producing a probe-bearing element of the invention.

FIG. 10 is a schematic view showing one of the steps in another exemplary method for producing a probe-bearing element of the invention. The probe-bearing element is made from a columnar block of glass, acrylic resin, metal or plastic. As shown in FIG. 10, a plurality of through holes 52 are provided through the columnar block 50 made of, for example, polypropylene with a laser processor 51. The plurality of through holes 52 are arranged in concentric circles or in a spiral. The diameter of the through holes 52 is about 10–100 μm.

Figure 11:
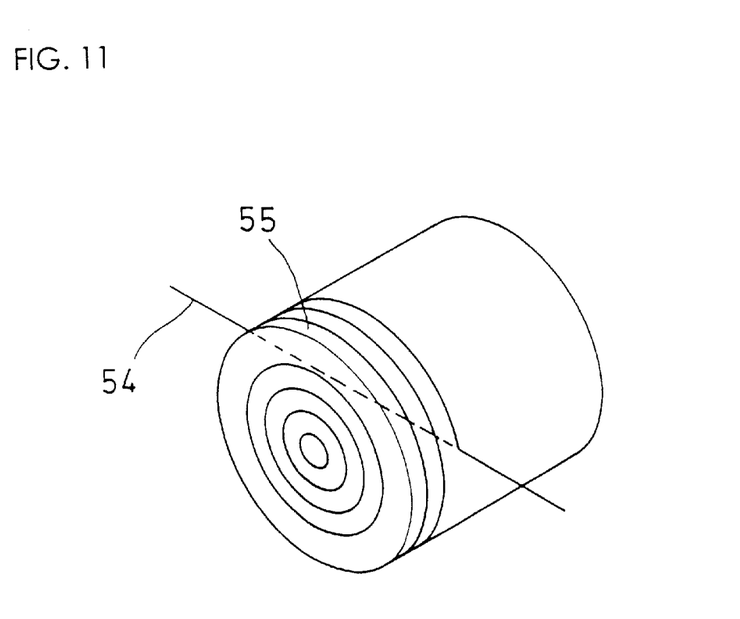
FIG. 11 is a schematic view showing one of the steps in another exemplary method for producing a probe-bearing element of the invention.

The inner walls of the through holes 52 are coated with poly-1-lysine or carbodiimide as described above. Then, probes such as DNA, protein and the like are injected into the through holes 52 to be bound thereto. The probes are injected as described above. As shown in FIG. 11, the columnar polypropylene block 50 injected with the probes is sliced into sheets with a thickness of about 100 μm by a laser beam 54 of a laser processor, a wire saw, a band saw, or the like. The sliced polypropylene sheets 55 are individually used as a probe-bearing element. The polypropylene sheet 55 may be used by itself or it may be adhered to a reinforcement member such as a glass, plastic or metal plate (thickness: 1–5 mm) as described with reference to FIG. 4. In this manner, identical probe-bearing elements with diverse probes at the same positions can be mass-produced.

According to the present invention, probe-bearing elements can be mass-produced at low cost with less time and trouble.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

All publications, including patent and patent application cited herein are incorporated herein by reference in their entirety.

What is claimed is:

1. A probe-bearing element comprising a sheet-like body having a plurality of through holes, wherein each of the plurality of through holes bears a biopolymer probe.

2. A probe-bearing element according to claim 1, wherein a thickness of the sheet-like body is 100 μm to 2 mm.

3. A probe-bearing element according to either claim 1 or 2, wherein the sheet-like body is mace of glass, acrylic resin, metal or plastic.

4. A probe-bearing element according to any one of claims 1 or 2, wherein each of the through holes has a diameter of 10 μm to 100 μm.

5. A probe-bearing element according to any one of claims 1 or 2, wherein the plurality of through holes are arranged in concentric circles or in a spiral.

6. A probe-bearing element according to any one of claims 1 or 2, wherein at least one of the probes borne in the through holes has a length of 200 bases or more.

7. A probe-bearing element according to any one of claims 1 or 2, wherein the probe is DNA, RNA or a protein.

8. A probe-bearing element according to any one of claims 1 or 2, wherein at least one surface of the sheet-like body is applied with an adhesive.

9. A method for producing a sheet-like probe-bearing element having a plurality of through holes bearing biopolymer probes, comprising the steps of:
providing a plurality of through holes through piled sheet-like bodies;
injecting a biopolymer probe into each of the through holes; and
separating the sheet-like bodies from each other.

10. A method for producing a sheet-like probe-bearing element having a plurality of through holes bearing biopolymer probes, comprising the steps of:

providing a plurality of through holes through a block-like material;
injecting a biopolymer probe into each of the through holes; and
slicing the block-like material into sheets such that every sheet has the plurality of through holes.

11. A method for producing a sheet-like probe-bearing element according to claim 9, wherein the step of providing a plurality of through holes employs laser irradiation.

12. A method for producing a sheet-like probe-bearing element according to claim 9, wherein prior to the step of injecting a biopolymer probe into each through hole, the through holes are pre-treated in order to promote binding between the through holes and the biopolymer probe.

13. A method for producing a sheet-like probe-bearing element according to claim 9, wherein the pretreatment is conducted by coating the through holes with poly-1-lysine or carbodiimide.

14. A probe-bearing element according to claim 3, wherein each of the through holes has a diameter of 10 μm to 100 μm.

15. A probe-bearing element according to claim 3, wherein the plurality of through holes are arranged in concentric circles or in a spiral.

16. A probe-bearing element according to claim 4, wherein the plurality of through holes are arranged in concentric circles or in a spiral.

17. A probe-bearing element according to claim 14, wherein the plurality of through holes are arranged in concentric circles or in a spiral.

18. A probe-bearing element according to claim 3, wherein at least one of the probes borne in the through holes has a length of 200 bases or more.

19. A probe-bearing element according to claim 4, wherein at least one of the probes borne in the through holes has a length of 200 bases or more.

20. A probe-bearing element according to claim 14, wherein at least one of the probes borne in the through holes has a length of 200 bases or more.

21. A probe-bearing element according to claim 15, wherein at least one of the probes borne in the through holes has a length of 200 bases or more.

22. A probe-bearing element according to claim 16, wherein at least one of the probes borne in the through holes has a length of 200 bases or more.

23. A probe-bearing element according to claim 17, wherein at least one of the probes borne in the through holes has a length of 200 bases or more.

24. A probe-bearing element according to claim 3, wherein the probe is DNA, RNA or a protein.

25. A probe-bearing element according to claim 4, wherein the probe is DNA, RNA or a protein.

26. A probe-bearing element according to claim 14, wherein the probe is DNA, RNA or a protein.

27. A probe-bearing element according to claim 15, wherein the probe is DNA, RNA or a protein.

28. A probe-bearing element according to claim 16, wherein the probe is DNA, RNA or a protein.

29. A probe-bearing element according to claim 17, wherein the probe is DNA, RNA or a protein.

30. A probe-bearing element according to claim 18, wherein the probe is DNA, RNA or a protein.

31. A probe-bearing element according to claim 19, wherein the probe is DNA, RNA or a protein.

32. A probe-bearing element according to claim 20, wherein the probe is DNA, RNA or a protein.

33. A probe-bearing element according to claim 21, wherein the probe is DNA, RNA or a protein.

34. A probe-bearing element according to claim 22, wherein the probe is DNA, RNA or a protein.

35. A probe-bearing element according to claim 23, wherein the probe is DNA, RNA or a protein.

36. A probe-bearing element according to claim 3, wherein at least one surface of the sheet-like body is applied with an adhesive.

37. A probe-bearing element according to claim 4, wherein at least one surface of the sheet-like body is applied with an adhesive.

38. A probe-bearing element according to claim 14, wherein at least one surface of the sheet-like body is applied with an adhesive.

39. A probe-bearing element according to claim 15, wherein at least one surface of the sheet-like body is applied with an adhesive.

40. A probe-bearing element according to claim 16, wherein at least one surface of the sheet-like body is applied with an adhesive.

41. A probe-bearing element according to claim 17, wherein at least one surface of the sheet-like body is applied with an adhesive.

42. A probe-bearing element according to claim 18, wherein at least one surface of the sheet-like body is applied with an adhesive.

43. A probe-bearing element according to claim 19, wherein at least one surface of the sheet-like body is applied with an adhesive.

44. A probe-bearing element according to claim 20, wherein at least one surface of the sheet-like body is applied with an adhesive.

45. A probe-bearing element according to claim 21, wherein at least one surface of the sheet-like body is applied with an adhesive.

46. A probe-bearing element according to claim 22, wherein at least one surface of the sheet-like body is applied with an adhesive.

47. A probe-bearing element according to claim 23, wherein at least one surface of the sheet-like body is applied with an adhesive.

48. A probe-bearing element according to claim 24, wherein at least one surface of the sheet-like body is applied with an adhesive.

49. A probe-bearing element according to claim 25, wherein at least one surface of the sheet-like body is applied with an adhesive.

50. A probe-bearing element according to claim 26, wherein at least one surface of the sheet-like body is applied with an adhesive.

51. A probe-bearing element according to claim 27, wherein at least one surface of the sheet-like body is applied with an adhesive.

52. A probe-bearing element according to claim 28, wherein at least one surface of the sheet-like body is applied with an adhesive.

53. A probe-bearing element according to claim 29, wherein at least one surface of the sheet-like body is applied with an adhesive.

54. A probe-bearing element according to claim 30, wherein at least one surface of the sheet-like body is applied with an adhesive.

55. A probe-bearing element according to claim 31, wherein at least one surface of the sheet-like body is applied with an adhesive.

56. A probe-bearing element according to claim 32, wherein at least one surface of the sheet-like body is applied with an adhesive.

57. A probe-bearing element according to claim 33, wherein at least one surface of the sheet-like body is applied with an adhesive.

58. A probe-bearing element according to claim 34, wherein at least one surface of the sheet-like body is applied with an adhesive.

59. A probe-bearing element according to claim 35, wherein at least one surface of the sheet-like body is applied with an adhesive.

60. A method for producing a sheet-like probe-bearing element according to claim 10, wherein the step of providing a plurality of through holes employs laser irradiation.

61. A method for producing a sheet-like probe-bearing element according to claim 10, wherein prior to the step of injecting a biopolymer probe into each through hole, the through holes are pre-treated in order to promote binding between the through holes and the biopolymer probe.

62. A method for producing a sheet-like probe-bearing element according to claim 11, wherein prior to the step of injecting a biopolymer probe into each through hole, the through holes are pre-treated in order to promote binding between the through holes and the biopolymer probe.

63. A method for producing a sheet-like probe-bearing element according to claim 60, wherein prior to the step of injecting a biopolymer probe into each through hole, the through holes are pre-treated in order to promote binding between the through holes and the biopolymer probe.

64. A method for producing a sheet-like probe-bearing element according to claim 10, wherein the pretreatment is conducted by coating the through holes with poly-1-lysine or carbodiimide.

65. A method for producing a sheet-like probe-bearing element according to claim 11, wherein the pretreatment is conducted by coating the through holes with poly-1-lysine or carbodiimide.

66. A method for producing a sheet-like probe-bearing element according to claim 12, wherein the pretreatment is conducted by coating the through holes with poly-1-lysine or carbodiimide.

67. A method for producing a sheet-like probe-bearing element according to claim 61, wherein the pretreatment is conducted by coating the through holes with poly-1-lysine or carbodiimide.

68. A method for producing a sheet-like probe-bearing element according to claim 62, wherein the pretreatment is conducted by coating the through holes with poly-1-lysine or carbodiimide.

69. A method for producing a sheet-like probe-bearing element according to claim 63, wherein the pretreatment is conducted by coating the through holes with poly-1-lysine or carbodiimide.

\* \* \* \* \*

UNITED STATES PATENT AND TRADEMARK OFFICE
CERTIFICATE OF CORRECTION

PATENT NO.   : 6,071,702
DATED        : June 6, 2000
INVENTOR(S)  : Kenji Yamamoto; Noriko Yurino; Hisanori Nasu It is certified that error appears in the above-identified patent and that said Letters Patent is hereby corrected as shown below:

<u>Title page,</u>
The spelling of the address of the Assignee should be corrected to read:
Hitachi Software Engineering Co.,
Ltd., Yokohama, Japan <u>Column 5, claim 3,</u>
Line 42, the word "mace" should be corrected to read -- made. --

Signed and Sealed this

Twentieth Day of November, 2001

*Attest:*

NICHOLAS P. GODICI
*Attesting Officer*    *Acting Director of the United States Patent and Trademark Office*